United States Patent
Zou et al.

(10) Patent No.: US 12,145,919 B2
(45) Date of Patent: *Nov. 19, 2024

(54) METHOD FOR PREPARING CHIRAL SYNTHETIC NICOTINE

(71) Applicant: SHENZHEN ZINWI BIO-TECH CO., LTD, Guangdong (CN)

(72) Inventors: Jun Zou, Guangdong (CN); Yang Zou, Guangdong (CN); Meisen Liu, Guangdong (CN); Weixian Luo, Guangdong (CN)

(73) Assignee: SHENZHEN ZINWI BIO-TECH CO., LTD, Guangdong (CN)

( * ) Notice: Subject to any disclaimer, the term of this patent is extended or adjusted under 35 U.S.C. 154(b) by 579 days.

This patent is subject to a terminal disclaimer.

(21) Appl. No.: 17/547,251

(22) Filed: Dec. 10, 2021

(65) Prior Publication Data

US 2023/0025652 A1    Jan. 26, 2023

Related U.S. Application Data

(63) Continuation of application No. PCT/CN2021/112799, filed on Aug. 16, 2021.

(30) Foreign Application Priority Data

Jul. 10, 2021 (CN) .......................... 202110781304.6

(51) Int. Cl.
C07B 53/00 (2006.01)
C07D 401/04 (2006.01)

(52) U.S. Cl.
CPC ............ *C07D 401/04* (2013.01); *C07B 53/00* (2013.01)

(58) Field of Classification Search
CPC .............................. C07D 401/04; C07B 53/00
See application file for complete search history.

(56) References Cited

FOREIGN PATENT DOCUMENTS

| | | |
|---|---|---|
| CN | 104341390 | 2/2015 |
| CN | 110256403 A | 9/2019 |
| CN | 111233829 | 6/2020 |
| CN | 111875620 A | 11/2020 |
| CN | 112876461 A | 6/2021 |
| WO | 2019037761 A1 | 2/2019 |

OTHER PUBLICATIONS

International Search Report cited in PCT/CN2020/112799 dated Apr. 6, 2022, 5 pages.
Sato, et al., "Psychotropic Agents. I Synthesis of 1-Pyridinyl-1-butanones, 1-Indolyl-1-butanones and the Related Compounds", vol. 26, 1978, 10 pages.
Shun-Ichi Murahashi et al., "Tungstate-catalyzed oxidation of secondary amines to nitrones. alpha.-Substitution of secondary amines via nitrones," Journal of Organic Chemistry, vol. 55, Mar. 1990, pp. 1736-1744.
Inn R. Baxendale et al., "Synthesis of nornicotine, nicotine and other functionalised derivatives using solid-supported reagents and scavengers," Journal of the Chemical Society—perkin Transactions 1, Jan. 2002, pp. 143-154.
Kun Huang et al., "A new and efficient approach to the synthesis of nicotine and anabasine analogues," Journal of Heterocyclic Chemistry, Nov. 2010, pp. 1-21.

*Primary Examiner* — Timothy R Rozof
(74) *Attorney, Agent, or Firm* — Cooper Legal Group, LLC

(57) ABSTRACT

A method for preparing chiral synthetic nicotine includes the following steps: Step S1. condensing nicotinic acid ester and γ-butyrolactone under the action of alkaline condensate in organic solvent I to obtain the first mixture; Step S2. performing a ring-opening reaction to the first mixture obtained in Step S1 by adding an acidic substance to obtain a second mixture; Step S3. separating 4-chloro-1-(3-pyridine)-1-butanone from the second mixture obtained in Step S2, reacting with chiral tert-butyl sulfinamide to obtain chiral N-(4-chloro-1-(pyridin-3-yl)butene)-2-methylpropane-2-sulfinamide; Step S4: reacting the chiral N-(4-chloro-1-(pyridin-3-yl) butene)-2-methylpropane-2-sulfenamide with a reducing agent, and then cyclizing under the action of hydrogen halide to obtain a chiral demethylized nicotine; and Step S5: performing methylamination to the chiral demethylized nicotine to obtain a chiral nicotine.

10 Claims, No Drawings

METHOD FOR PREPARING CHIRAL SYNTHETIC NICOTINE

CROSS-REFERENCE TO RELATED APPLICATION

This application is a continuation of international application of PCT application serial no. PCT/CN2021/112799 filed on Aug. 16, 2021, which claims the priority benefit of China application no. 202110781304.6, filed on Jul. 10, 2021. The entirety of each of the above mentioned patent applications is hereby incorporated by reference herein and made a part of this specification.

BACKGROUND

Technical Field

The invention relates to the technical field of chemical synthesis, and, in particular, to a method for preparing chiral synthetic nicotine.

In recent years, with the rapid development of electronic cigarette industry, nicotine, as one of the important active components of e-cigarette, is in increasing demand. Nicotine is mainly obtained from tobacco extract and artificial chemical synthesis methods. However, nicotine extracted and purified from tobacco or other plants also contains other impurities such as carcinogenic tobacco compounds, which is harmful to human health. Moreover, tobacco extract is susceptible to raw materials and climate, rendering the large scale production thereof difficult. Chemically synthesized nicotine contains nearly no other impurities such s carcinogenic tobacco compounds, being suitable for large-scale industrial production, and thus is attracting extensive attention.

In particular, a preparation method of racemic nicotine is reported in the *Journal of Organic Chemistry*, 1990, 55 (6), 1736-44, which synthesizes racemic nicotine by using pyrrolidine as the starting material via a four-step process, as shown in reaction formula 1:

Reaction Formula 1

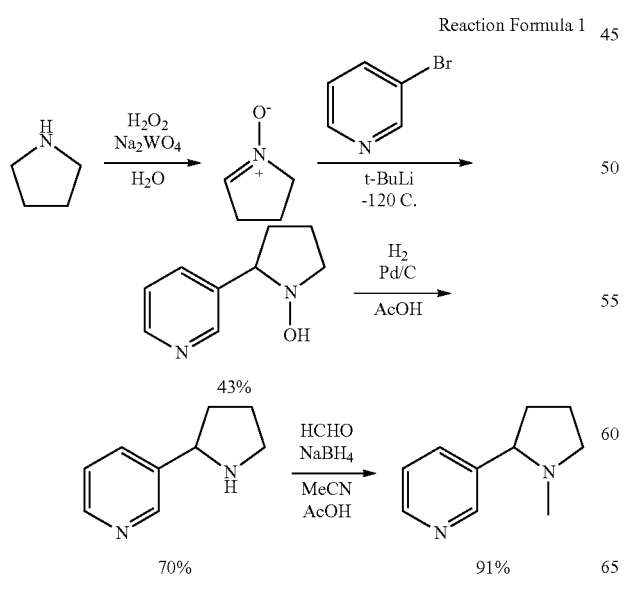

However, the preparation method based on reaction formula 1 requires harsh reaction conditions, gives a relatively low yield, and obtains racemic nicotine.

A method for preparing racemic nicotine by using nicotinic acid as a starting material is reported in *Journal of the Chemical Society*, Perkin Transactions 1 (2002), (2), 143-154, as shown in reaction formula 2:

Reaction Formula 2

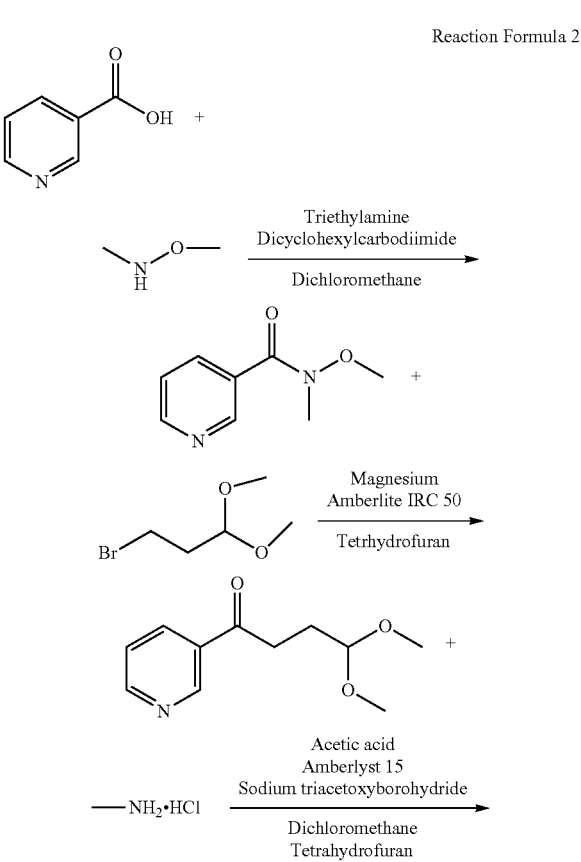

In the method based on reaction formula 2, a Grignard reagent is required, and the resultant is also racemic nicotine.

A method for preparing nicotine from 3-Br-pyridine as a raw material is reported in *Journal of Heterocyclic Chemistry*, 2009, 46(6), 1252-1258, as shown in reaction formula 3:

Reaction Formula 3

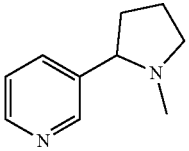
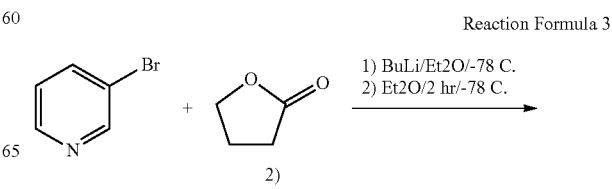

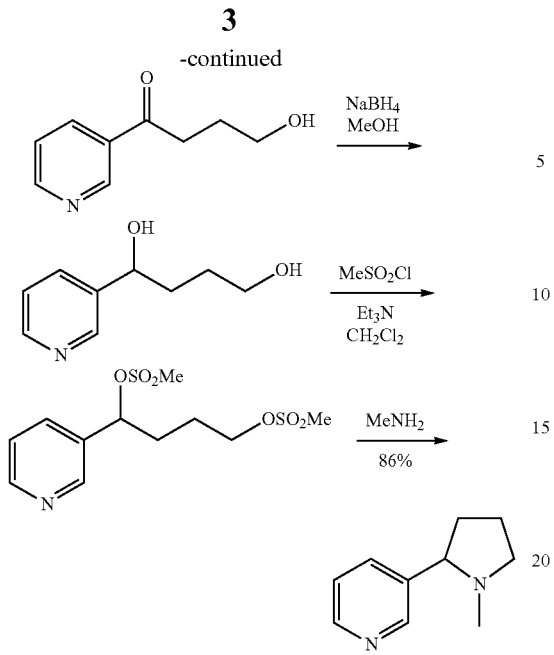

The preparation method based on reaction formula 3 uses 3-Br-pyridine as the raw material, requires a harsh experimental condition of ultra low temperature (−78° C.), which is not suitable for industrial production, and gives racemic nicotine.

At present, there are few studies on the preparation methods for chiral synthetic nicotine. The chiral synthetic nicotine is basically obtained by chiral resolution, but the chiral resolution reagent is expensive and is not conducive to industrial production. Therefore, it is important to study the preparation method of chiral synthetic nicotine.

The patent Publication No. CN104341390A discloses a preparation method of s-nicotine, which uses a cyclic imine as the starting material, but requires expensive chiral catalyst and high-pressure hydrogen equipment causing high production cost, and thus is not suitable for large-scale industrial production. The patent Publication No. CN111233829A discloses a preparation method of optically active nicotine, in which an organic metal catalyst is prepared by using chiral ligands containing nitrogen or phosphorus, and imine salt derivatives are used as the starting material to prepare chiral synthetic nicotine. However, the preparation of the organic metal catalyst is complex, the production cost is high, and the yield and purity of the chiral synthetic nicotine are low.

Therefore, the present application provides a novel method for preparing chiral synthetic nicotine, which utilizes more cheap and readily available raw materials and involves in simpler operations.

SUMMARY

In order to improve the yield and purity of chiral synthetic nicotine and reduce the cost, the present application provides a method for preparing chiral synthetic nicotine.

In a first aspect, the present application provides a method for preparing chiral synthetic nicotine, which is realized by the following technical solutions.

A method for preparing chiral synthetic nicotine includes the following steps:

Step S1. condensing nicotinic acid ester and γ-butyrolactone under the action of alkaline condensate in organic solvent I to obtain the first mixture;

Step S2. performing a ring-opening reaction to the first mixture obtained in Step S1 by adding an acidic substance to obtain a second mixture;

Step S3. separating 4-chloro-1-(3-pyridine)-1-butanone from the second mixture obtained in Step S2, reacting 4-chloro-1-(3-pyridine)-1-butanone with chiral tert-butyl sulfinamide in organic solvent II and titanate to obtain a third mixture containing chiral n-(4-chloro-1-(pyridin-3-yl)butene)-2-methylpropane-2-sulfinamide, filtering, extracting, and removing the solvent to obtain chiral n-(4-chloro-1-(pyridin-3-yl)butene)-2-methylpropane-2-sulfenamide;

Step S4: dissolving the chiral n-(4-chloro-1-(pyridin-3-yl)butene)-2-methylpropane-2-sulfenamide obtained in Step S3 in organic solvent III, reacting with a reducing agent, and then cyclizing under the action of hydrogen halide to obtain a fourth mixture; and Step S5; reacting the fourth mixture obtained in Step S4 with a methylamination reagent to obtain a fifth mixture, and purifying the fifth mixture to obtain the chiral nicotine.

In the above technical solution, the present application adopts nicotinic acid ester and γ-butyrolactone, which are cheap and readily available, as raw materials, and significantly reduces the production cost of chiral nicotine. In this application, a target chiral center is constructed by using the chiral steric hindrance of the chiral tert-butyl sulfenamide, so that the chiral amino group is induced by the chiral-tert butyl sulfenamide, then cyclization is initiated to construct a chiral demethylnicotine, and finally methylamination is performed to provide the nicotine with single configuration. The preparation method of the chiral synthetic nicotine according to the present application has the advantages of simple steps, easy operation, high yield and mild reaction conditions, providing nicotine with a single configuration and high EE value, and thus is suitable for industrial production.

Preferably, in Step S1, the molar ratio of nicotinic acid ester, γ-butyrolactone, and alkaline condensate is 1:(1-2):(1.2-3). More preferably, the molar ratio of nicotinic acid ester, γ-butyrolactone, and alkaline condensate is 1:1:3.

In the present application, the nicotinic acid ester is selected from a group consisting of methyl nicotinate and ethyl nicotinate.

Preferably, in Step S1, the alkaline condensate is one or more selected from a group consisting of alkali metal alkoxide, alkaline earth metal hydride, alkaline earth metal oxide, amine, metal salt of amines, hydroxide, carbonate and bicarbonate.

In the present application, the alkali metal alkoxide includes, but not limited to, any one selected for the group consisting of sodium tert-butoxide, sodium methoxide, sodium ethoxide and potassium tert-butoxide.

In the present application, the alkaline earth metal hydride includes, but not limited to, one or more selected from a group consisting of NaH, LiH and KH.

In the present application, the alkaline earth metal oxide includes, but not limited to, one or more selected from a group consisting of $Na_2O$, $Li_2O$ and $K_2O$.

In the present application, the amines include, but not limited to, triethylamine and/or diisopropyl ethyl amine.

In the present application, the metal salt of the amine includes, but not limited to, sodium bis(trimethylsilyl)amide and/or lithium diisopropyl amide.

In the present application, the hydroxide includes, but not limited to, one or more selected from a group consisting of sodium hydroxide, lithium hydroxide and magnesium hydroxide.

In the present application, the carbonate includes, but not limited to, one or more selected from a group consisting of sodium carbonate, potassium carbonate and cesium carbonate.

In the present application, the bicarbonate includes, but not limited to, sodium bicarbonate and/or potassium bicarbonate.

More preferably, the alkaline condensate is any one selected from a group consisting of sodium tert-butanol, NaH and potassium tert-butoxide; and most preferably, the alkaline condensate is NaH.

In the present application, in Step S1, the reaction is carried out in $N_2$ atmosphere, and the γ-butyrolactone and alkaline condensate are added in the order of first γ-butyrolactone, then alkaline condensate, and finally nicotinic acid ester.

In the present application, a reaction temperature of γ-butyrolactone and alkaline condensate is 0° C., with a reaction time of 30 min; and a reaction temperature of added nicotinic acid ester with γ-butyrolactone and alkaline condensate is 25° C., with a reaction time of 1 h.

In the present application, in Step S1, the organic solvent I is anhydrous tetrahydrofuran.

In the present application, in Step S1, the first mixture contains a condensation product produced by the condensation reaction of nicotinic acid ester and γ-butyrolactone.

In the present application, in particular, Step S2 includes the following steps of: acidifying the first mixture in Step S1 to a system pH value of 6-7, adding acidic substances, refluxing at 75-85° C. for 6-10 h, and ring opening to obtain the second mixture. Preferably, Step S2 includes the steps of: acidifying the first mixture in Step S1 to a system pH value of 6, adding acidic substances, refluxing at 80° C. for 8 h, and ring opening to obtain the second mixture.

Preferably, in Step S2, the acidic substance is one or more selected from a group consisting of hydrochloric acid, sulfuric acid, phosphoric acid, nitric acid, hydrobromic acid, hydroiodic acid, perchloric acid, trifluoromethanesulfonic acid, trifluoroacetic acid, trichloroacetic acid, citric acid, tartaric acid and maleic acid; and, more preferably, the acidic substance is hydrochloric acid.

In the present application, the acidic substance has a concentration of 12 mol/L.

In the present application, in Step S2, the molar ratio of the acidic substance to the condensation product in the first mixture is (1-100):1; preferably, the molar ratio of the acidic substance to the condensation product in the first mixture is (1-5):1; and more preferably, the molar ratio of the acidic substance to the condensation product in the first mixture is 1:1.

In the present application, in Step S2, a refluxing temperature is 50-300° C.; and, preferably, the refluxing temperature is 80° C.

In the present application, in Step S3, in particular, separating 4-chloro-1-(3-pyridine)-1-butanone from the second mixture obtained in Step S2 includes the steps of: adjusting the pH value of the second mixture to 6-7, extracting, combining organic phases, removing water from the organic phase, and spin drying the solvent to obtain 4-chloro-1-(3-pyridine)-1-butanone; and preferably, separating 4-chloro-1-(3-pyridine)-1-butanone from the second mixture obtained in Step S2 includes the steps of: adding alkali to adjust the pH value of the second mixture to 7, extracting with ethyl acetate-water (the volume ratio of ethyl acetate to water is 1:2) for 3 times, combine the organic phases, drying the organic phase by anhydrous $MgSO_4$, and spin drying the solvent to obtain 4-chloro-1-(3-pyridine)-1-butanone.

Preferably, in Step S3, the molar ratio of the 4-chloro-1-(3-pyridine)-1-butanone to the chiral tert-butyl sulfenamide is 1: (1-2.5); and, more preferably, the molar ratio of the 4-chloro-1-(3-pyridine)-1-butanone to chiral tert-butyl sulfinamide is 1:2.

Preferably, in Step S3, the chiral tert-butyl sulfenamide is S-tert-butyl sulfenamide, and in Step S5, the chiral nicotine is S-nicotine.

Preferably, in Step S3, the chiral tert-butyl sulfenamide is R-tert-butyl sulfenamide, and in Step S5, the chiral nicotine is R-nicotine.

Preferably, in Step S3, the organic solvent II is one or more selected from a group consisting of anhydrous tetrahydrofuran, dimethyltetrahydrofuran and 1,4-dioxane; and, more preferably, the organic solvent II is anhydrous tetrahydrofuran.

In the present application, the anhydrous tetrahydrofuran, dimethyltetrahydrofuran and 1,4-dioxane are solvents with a boiling point higher than 75° C., which can improve the yield of the reaction between 4-chloro-1-(3-pyridine)-1-butanone and chiral tert-butyl Sulfinamide.

Preferably, in Step S3, a reaction temperature of the 4-chloro-1-(3-pyridine)-1-butanone and chiral tert-butyl sulfenamide is 70-90° C., with a reaction time of 5-8 h; and, more preferably, the reaction temperature of the 4-chloro-1-(3-pyridine)-1-butanone and chiral tert-butyl sulfenamide is 70° C., with a reaction time of 6 h.

In the present application, in Step S3, the titanate is any one selected from a group consisting of tetraethyl titanate, tetrabutyl titanate and tetraisopropyl titanate; and, preferably, the titanate is tetraethyl titanate.

In the present application, in Step S3, the molar ratio of the titanate to the chiral tert-butyl sulfenamide is (2-3):1; and, preferably, the molar ratio of the titanate to chiral tert-butyl sulfenamide is 2:1.

In the present application, in Step S3, a reaction temperature of the reaction between the 4-chloro-1-(3-pyridine)-1-butanone and chiral tert-butyl sulphonamide is 65-75° C., with a reaction time of 4-8h; and, preferably, the reaction temperature of the 4-chloro-1-(3-pyridine)-1-butanone and chiral tert-butyl sulfenamide is 70° C., with a reaction time of 6 h.

In the present application, in Step S3, the reaction of the 4-chloro-1-(3-pyridine)-1-butanone and chiral tert-butyl sulfenamide is quenched with saturated salt water.

In the present application, in Step S3, a post-treatment step is performed after the quenching, which, in particular, includes the steps of: filtering to obtain a filter cake and a filtrate, washing the filter cake with ethyl acetate, collecting the filtrate, combine the filtrates, extracting with saturated salt water to obtain a water layer, extracting the water layer with ethyl acetate, collecting the organic phase, drying with anhydrous $MgSO_4$ and concentrating in vacuum to obtain N-(4-chloro-1-(pyridin-3-yl)butene)-2-methylpropane-2-sulfenamide.

In the present application, in Step S4, the chiral N-(4-chloro-1-(pyridin-3-yl)butene)-2-methylpropane-2-sulfenamide obtained in Step 3 is dissolved in a solvent before reacting with a reducing agent, and the solvent includes, but not limited to, absolute ethanol.

Preferably, in Step S4, the reducing agent is one or more selected from a group consisting of metal borohydride, iron, zinc, hydrogen, ferrous chloride, zinc (I) chloride, stannous chloride and lithium aluminum tetrahydride.

In the present application, the metal borohydride includes, but not limited to, one or more selected from a group consisting of sodium borohydride, potassium borohydride and sodium cyanobohydride borane.

More preferably, the reducing agent is one or more selected from a group consisting of sodium borohydride, potassium borohydride, lithium aluminum tetrahydride, iron powder, zinc powder and stannous chloride.

Most preferably, the reducing agent is sodium borohydride.

In the present application, in Step S4, the organic solvent III includes, but not limited to, 1,4-dioxane.

In the present application, in Step S4, the molar ratio of the chiral N-(4-chloro-1-(pyridin-3-yl)butene)-2-methylpropane-2-sulfenamide to the reducing agent is 1: (1.1-1.5); and, more preferably, the molar ratio of the chiral N-(4-chloro-1-(pyridin-3-yl)butene)-2-methylpropane-2-sulfenamide to the reducing agent is 1:1.2.

In the present application, in Step S4, the reaction temperature between the chiral and the reducing agent is −30° C.-10° C., and the reaction time is 2-4 h. Preferably, the reaction temperature of the chiral N-(4-chloro-1-(pyridin-3-yl)butene)-2-methylpropane-2-sulfenamide with the reducing agent is 0° C., and the reaction time is 3 h.

In the present application, in Step S4, after the chiral N-(4-chloro-1-(pyridin-3-yl) butene)-2-methylpropane-2-sulfenamide reacts with the reducing agent, the system is adjusted with dilute acid to an extent that no foaming occurs. The dilute acid includes, but not limited to, dilute hydrochloric acid, and the concentration of the dilute hydrochloric acid can be 0.1 mol/l.

In the present application, in Step S4, the molar ratio of the hydrogen halide to chiral N-(4-chloro-1-(pyridin-3-yl) butene)-2-methylpropane -2- sulfenamide is (1.5-2.5):1. Preferably, the molar ratio of the hydrogen halide to chiral N-(4-chloro-1-(pyridin-3-yl)butene)-2-methylpropane-2-sulfenamide is 2:1.

In the present application, in Step S4, the hydrogen halide is any one selected from a group consisting of HCl, HBr, HF and HI. Preferably, the hydrogen halide is HBr.

In the present application, in step S4, the condition for cyclizing under the action of hydrogen halide includes performing a reflux reaction for 6-10 h. Preferably, the condition for cyclizing under the action of hydrogen halide includes performing the reflux reaction for 8 h.

In the present application, in Step S4, a temperature of the reflux reaction is 70-90° C. More preferably, the temperature of the reflux reaction is 80° C.

In the present application, in Step S4, after the reflux reaction, the system is adjusted to a pH of 7 by using an alkali, and then extracted with ethyl acetate-water (the volume ratio of ethyl acetate to water is 1:2) to obtain the fourth mixture. In particular, the alkali includes, but not limited to, 52 wt % NaOH aqueous solution.

In the present application, the fourth mixture obtained in Step S4 contains chiral demethylnicotine.

In the present application, in Step S5, a reaction temperature of the fourth mixture with the methylamination reagent is 70-90° C., and a reaction time is 6-10 h. Preferably, the reaction temperature of the fourth mixture with the methylamination reagent is 80° C., and the reaction time is 8 h.

In the present application, in Step S5, the methylamination reagent is formic acid and formaldehyde.

In the present application, in Step S5, the molar ratio of the formic acid, formaldehyde and chiral demethylnicotine in the fourth mixture in Step 4 is (1.6-2):(1.05-1.2):1. Preferably, the molar ratio of the formic acid, formaldehyde and chiral demethylnicotine in the fourth mixture in Step S4 is 1.8:1.1:1.

In the present application, in Step S5, purifying the fifth mixture particularly includes: cooling the fifth mixture to 20-30° C., adding water and an aqueous solution of hydrochloric acid, and then extracting with dichloromethane. The resulting aqueous phase is adjusted to a pH value of 11 by using an alkali, and extracted with dichloromethane for 3 times. The resulting organic phases from 4 extractions are combined, dried with $Na_2SO_4$ and concentrated under reduced pressure to obtain a crude chiral nicotine, which is purified by distillation to obtain the chiral nicotine.

In summary, the present application achieves the following beneficial effects.

1. Nicotinic acid ester and γ-butyrolactone, as staring materials, used in the present application are cheap and readily available, eliminating the problem of high cost suffered in chiral synthesis of nicotine. As a completely new preparation method of chiral synthetic nicotine, inducing a chiral amino groups in a chiral tert-butyl sulfenamide and then constructing a target chiral center by cyclization can provide a chiral synthetic nicotine with a single configuration by a high yield and a high EE value.

2. The preparation process in the application involves in simple process, mild reaction conditions, easy operation, a wide source of raw materials, low cost, and a resulting chiral synthetic nicotine with high impurity, without other harmful tobacco compounds, and thus is especially suitable for large-scale industrial production of chiral synthetic nicotine.

DESCRIPTION OF THE EMBODIMENTS

The present application will be further described in detail below in combination with examples.

The raw materials used in this application can be commercially obtained. Unless otherwise specified, the raw materials not mentioned in examples and comparison examples in this application are purchased from Sinopharm Chemical Reagent Co., Ltd.

EXAMPLES

Examples 1-16 provide a preparation method of chiral synthetic nicotine, which is described below with Example 1 as an example.

Example 1 provided a preparation method of chiral synthetic nicotine (S-nicotine). In particular, the nicotinic acid ester is methyl nicotinate, synthesized by the reaction in reaction formula 4:

Reaction formula 4

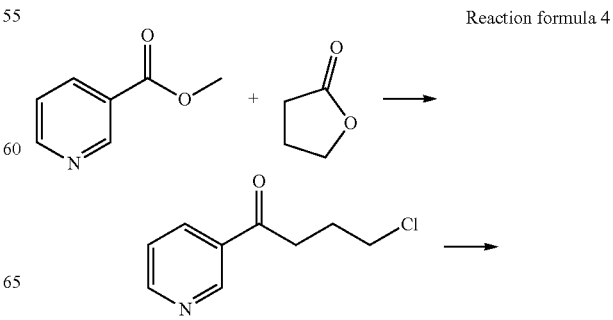

-continued

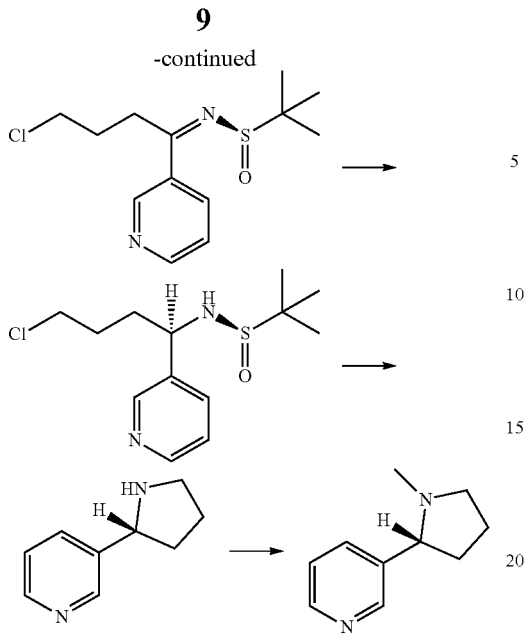

The preparation steps particularly included:

Step S1. Dissolving 86.1 g (1 mol, 1 eq) γ-butyrolactone (CAS No. 96-48-0) in 2 L anhydrous tetrahydrofuran under the protection of $N_2$ at 0° C., stirring at a speed of 600 rpm, adding 72 g (3 mol, 3 eq) NaH to react at 0° C. for 0.5 h, adding 137.1 g (1 mol) methyl nicotinate (CAS No. 93-60-7) after reaction, and reacting at 25° C. for 1 h to complete the condensation reaction and obtain the first mixture;

Step S2. Adjusting the first mixture prepared in Step S1 to a system pH value of 6 by using 12 mol/L hydrochloric acid, then adding 0.083 L 12 mol/L hydrochloric acid (1 mol, 1 eq), refluxing at 80° C. for 8 h to perform ring opening in the condensation product in the first mixture to obtain the second mixture;

Step S3. Adjusting the pH of the second mixture prepared in Step S2 to 7 by using 52 wt % NaOH aqueous solution, extracting with ethyl acetate-water (the volume of ethyl acetate and water is 1:2) for three times, combining the organic phases, adding anhydrous $MgSO_4$ to the organic phase, dry spinning the solvent to obtain 4-chloro-1-(3-pyridine)-1-butanone; then, adding 4-chloro-1-(3-pyridine)-1-butanone and 242.4 g (2 mol, 2 eq) S-tert-butyl sulfenamide to 7 L anhydrous tetrahydrofuran, stirring at a speed of 600 rpm, adding 456.3 g (2 mol, 2 eq) tetraethyl titanate, stirring at 70° C. to react for 6 h, and adding 50 ml saturated salt water to quench the reaction to obtain the third mixture; filtering the third mixture to obtain a filtrate, washing the filter cake with ethyl acetate, combining the filtrate, extracting with saturated salt water to obtain an aqueous layer, extracting the aqueous layer with ethyl acetate to obtain an organic phase, drying the organic phase with anhydrous $MgSO_4$, filtering to remove anhydrous $MgSO_4$ to obtain the filtrate, and vacuum concentrating the filtrate to remove the solvent and obtain (S, Z)-N-(4-chloro-1-(pyridin-3-yl)butene)-2-methylpropane-2-sulfenamide;

Step S4. Dissolving (S, Z)-N-(4-chloro-1-(pyridin-3-yl)butene)-2-methylpropane-2-sulfenamide prepared in Step S3 in 2 L 1,4-dioxane, adding 45.4 g (1.2 mol, 1.2 eq) sodium borohydride at 0° C., stirring at 600 rpm to react for 3 hours to obtain a mixture containing (S)-N-((S)-4-chloro-1-(pyridin-3-yl)butyl)-2-methylpropane-2-thionamide; then adding 12 mol/L hydrochloric acid to the mixture containing (S)-N-((S)-4-chloro-1-(pyridin-3-yl)butyl)-2-methylpropane-2-thionamide to adjust the reaction system until no foaming occurs, adding 161.8 g (2 mol, 2 eq) HBr, refluxing at 80° C. for 8 h, adjust the pH of the system to 7 by using 52 wt % NaOH aqueous solution, and then extracting with ethyl acetate-water (the volume ratio of ethyl acetate to water is 1:2) to obtain a fourth mixture; and Step S5. Preparing 37 wt % aqueous formaldehyde solution by using 33 g (1.1 mol, 1.1 eq) formaldehyde; adding 82.7 g (1.8 mol, 1.8 eq) formic acid to the fourth mixture prepared in Step S4, mixing evenly, heating to 80° C., reacting at 80° C. for 8 h, then cooling to 25° C., add 0.083 L 12 mol/l aqueous hydrochloric acid solution, extracting with dichloromethane to obtain an aqueous phase, adjusting the pH of the aqueous phase to 11 by using 52 wt % aqueous NaOH solution, extracting the adjusted aqueous phase with dichloromethane for three times, combining the organic phases, adding $Na_2SO_4$ to dry the organic phase, concentrating under reduced pressure to remove the solvent to obtain crude S-nicotine, and purifying the crude S-nicotine by subjecting to one atmospheric distillation to obtain S-nicotine, with a yield of 74%, an EE value of 99% and a purity of 98%.

It should be noted that, the mass and specific moles involved in the example in the application can be selected according to the size of the industrialized container, as long as the equivalence ratios between individual reaction raw materials are kept.

Examples 2-3 differ from Example 1 only in that the type of alkaline condensate is adjusted in the reaction in Step S1, as shown in Table 1.

TABLE 1

Effect of the selected alkaline condensates on the reaction in Step S1

| No. | Alkaline Condensates | Yield of S-nicotine (%) |
|---|---|---|
| Example 1 | NaH | 74 |
| Example 2 | Sodium tert-butoxide | 68 |
| Example 3 | Potassium tert-butoxide | 65 |

Examples 4-5 differ from Example 1 only in that, in Step S1, the amount of methyl nicotinate, γ-butyrolactone and NaH as used is shown in Table 2.

TABLE 2

Effect of the amount of materials on the reaction in Step S1

| No. | Equivalent quantity of methyl nicotinate (eq) | Equivalent quantity of γ-butyrolactone (eq) | Equivalent quantity of NaH (eq) | Yield of S-nicotine (%) |
|---|---|---|---|---|
| Example 1 | 1 | 1 | 3 | 74 |
| Example 4 | 1 | 2 | 1.2 | 68 |
| Example 5 | 1 | 1 | 1.5 | 70 |

Examples 6-8 differ from Example 1 only in that, the organic solvent II is adjusted in Step S3, as shown in Table 3.

TABLE 3

Effect of selected organic solvent II on the reaction in Step S3

| No. | Organic solvents | Yield of S-nicotine(%) |
|---|---|---|
| Example 1 | Anhydrous tetrahydrofuran | 74 |
| Example 6 | Methyl tert-butyl ether | 0 |
| Example 7 | 1,4-dioxane | 52 |
| Example 8 | Dimethyl tetrahydrofuran | 70 |

Examples 9-11 differ from Example 1 only in that, the amount of S-tert-butyl sulfenamide is adjusted in Step S3, as shown in Table 4.

TABLE 4

Effect of amount of S-tert-butylsul sulfenamide in Step S3 on the reaction

| No. | Equivalent quantity of S-tert-butylsul sulfenamide (eq) | Yield of S-nicotine (%) |
|---|---|---|
| Example 1 | 2 | 74 |
| Example 9 | 1.5 | 70 |
| Example 10 | 1 | 63 |
| Example 11 | 2.5 | 72 |

Examples 12-14 differ from Example 1 only in that, in Step S3, the reaction temperature and time are adjusted, as shown in Table 5.

TABLE 5

Effects of reaction temperature and time on reaction in Step S3

| No. | Reaction temperature (° C.) | Reaction time (h) | Yield of S-nicotine (%) |
|---|---|---|---|
| Example 1 | 70 | 6 | 74 |
| Example 12 | 90 | 5 | 66 |
| Example 13 | 70 | 8 | 72 |
| Example 14 | 60 | 8 | 70 |

Example 15 differs from Example 1 only in that, in Step S1, methyl nicotinate is equimolar replaced with ethyl nicotinate (CAS No. 614-18-6), and the yield of S-nicotine is 73%, the EE value is 99%, and the purity is 98%.

Example 16 differs from example 1 only in that, the S-tert-butyl sulfenamide is equimolar replaced with R-tert-butyl sulfenamide, and the yield of r-nicotine is 72%, the EE value is 99%, and the purity is 98%.

The specific embodiment is only an interpretation of the application and is not a limitation to the present application. After reading the specification, those skilled in the art can make modifications to the embodiment without creative contribution as needed, but they are protected by the patent law as long as they are within the scope of the claims of the application.

What is claimed is:

1. A method for preparing a chiral synthetic nicotine, comprising the following steps:
   step S1, condensing nicotinic acid ester and γ-butyrolactone under an action of alkaline condensate in an organic solvent I to obtain a first mixture;
   step S2, performing a ring-opening reaction to the first mixture obtained in the step S1 by adding an acidic substance to obtain a second mixture;
   step S3, separating 4-chloro-1-(3-pyridine)-1-butanone from the second mixture obtained in the step S2, reacting 4-chloro-1-(3-pyridine)-1-butanone with a chiral tert-butyl sulfinamide in an organic solvent II and titanate to obtain a third mixture containing a chiral n-(4-chloro-1-(pyridin-3-yl)butene)-2-methylpropane-2-sulfinamide, filtering, extracting, and removing the organic solvent II to obtain a chiral n-(4-chloro-1-(pyridin-3-yl)butene)-2-methylpropane-2-sulfenamide;
   step S4, dissolving the chiral n-(4-chloro-1-(pyridin-3-yl)butene)-2-methylpropane-2-sulfenamide obtained in the step S3 in an organic solvent III, reacting with a reducing agent, and then cyclizing under an action of hydrogen halide to obtain a fourth mixture; and
   step S5, reacting the fourth mixture obtained in the step S4 with a methylamination reagent to obtain a fifth mixture, and purifying the fifth mixture to obtain the chiral synthetic nicotine.

2. The method for preparing the chiral synthetic nicotine according to claim 1, wherein, in the step S3, the chiral tert-butyl sulfenamide is S-tert-butyl sulfenamide, and in the step S5, the chiral nicotine is S-nicotine.

3. The method for preparing the chiral synthetic nicotine according to claim 1, wherein, in the step S3, the chiral tert-butyl sulfenamide is R-tert-butyl sulfenamide, and in the step S5, the chiral nicotine is R-nicotine.

4. The method for preparing the chiral synthetic nicotine according to claim 1, wherein, in the step S3, the organic solvent II is one or more selected from a group consisting of anhydrous tetrahydrofuran, dimethyltetrahydrofuran and 1,4-dioxane.

5. The method for preparing the chiral synthetic nicotine according to claim 4, wherein, in the step S3, a reaction temperature of the 4-chloro-1-(3-pyridine)-1-butanone and the chiral tert-butyl sulfenamide is 70-90° C., with a reaction time of 5-8 h.

6. The method for preparing the chiral synthetic nicotine according to claim 1, wherein, in the step S3, a molar ratio of the 4-chloro-1-(3-pyridine)-1-butanone to the chiral tert-butyl sulfenamide is 1:(1-2.5).

7. The method for preparing the chiral synthetic nicotine according to claim 1, wherein, in the step S1, a molar ratio of nicotinic acid ester, γ-butyrolactone, and the alkaline condensate is 1:(1-2):(1.2-3).

8. The method for preparing the chiral synthetic nicotine according to claim 1, wherein, in the step S1, the alkaline condensate is one or more selected from a group consisting of alkali metal alkoxide, alkaline earth metal hydride, alkaline earth metal oxide, amine, metal salt of amines, hydroxide, carbonate and bicarbonate.

9. The method for preparing the chiral synthetic nicotine according to claim 1, wherein, in the step S2, the acidic substance is one or more selected from a group consisting of hydrochloric acid, sulfuric acid, phosphoric acid, nitric acid, hydrobromic acid, hydroiodic acid, perchloric acid, trifluoromethanesulfonic acid, trifluoroacetic acid, trichloroacetic acid, citric acid, tartaric acid and maleic acid.

10. The method for preparing the chiral synthetic nicotine according to claim 1, wherein, in the step S4, the reducing agent is one or more selected from a group consisting of metal borohydride, iron, zinc, hydrogen, ferrous chloride, zinc (I) chloride, stannous chloride and lithium aluminum tetrahydride.

* * * * *